US012041960B2

(12) United States Patent
Ballesteros Gomez et al.

(10) Patent No.: US 12,041,960 B2
(45) Date of Patent: Jul. 23, 2024

(54) METHOD OF GENERATING AEROSOL

(71) Applicant: NICOVENTURES TRADING LIMITED, London (GB)

(72) Inventors: Pablo Javier Ballesteros Gomez, London (GB); Jeremy Philips, London (GB)

(73) Assignee: NICOVENTURES TRADING LIMITED, London (GB)

( * ) Notice: Subject to any disclaimer, the term of this patent is extended or adjusted under 35 U.S.C. 154(b) by 35 days.

(21) Appl. No.: 17/447,900

(22) Filed: Sep. 16, 2021

(65) Prior Publication Data

US 2022/0001120 A1  Jan. 6, 2022

Related U.S. Application Data

(62) Division of application No. 16/320,598, filed as application No. PCT/EP2017/068804 on Jul. 25, 2017, now Pat. No. 11,141,548.

(30) Foreign Application Priority Data

Jul. 26, 2016 (GB) ..................................... 1612945

(51) Int. Cl.
*A61M 11/04* (2006.01)
*A24B 15/16* (2020.01)
(Continued)

(52) U.S. Cl.
CPC .......... *A24B 15/167* (2016.11); *A24B 15/165* (2013.01); *A24D 1/002* (2013.01);
(Continued)

(58) Field of Classification Search
None
See application file for complete search history.

(56) References Cited

U.S. PATENT DOCUMENTS

| 174,884 A | 3/1876 | Wolff |
| 239,198 A | 3/1881 | Simonds |

(Continued)

FOREIGN PATENT DOCUMENTS

| CN | 86102917 A | 11/1987 |
| CN | 1040914 A | 4/1990 |

(Continued)

OTHER PUBLICATIONS

Application and File History for U.S. Appl. No. 29/676,726, filed Jan. 14, 2019, 98 pages, inventor(s): Powell et al.

(Continued)

*Primary Examiner* — Dennis R Cordray
(74) *Attorney, Agent, or Firm* — Husch Blackwell LLP

(57) ABSTRACT

Provided herein is a method of generating aerosol from an aerosol-generating substrate using an aerosol-generating device with at least one heat source disposed to heat, but not burn, the aerosol-generating substrate in use. The aerosol-generating substrate has first and second portions having substantially the same composition, and/or has first and second portions and there is no physical separation between the portions. The method includes heating the aerosol-generating substrate in the aerosol-generating device, so that a temperature profile of the first portion of the aerosol-generating substrate during heating is different from a temperature profile of the second portion of the aerosol-generating substrate.

14 Claims, 3 Drawing Sheets

(51) Int. Cl.
   *A24B 15/167* (2020.01)
   *A24D 1/00* (2020.01)
   *A24D 1/20* (2020.01)
   *A24F 40/20* (2020.01)
   *A24F 40/46* (2020.01)
   *A61M 15/06* (2006.01)

(52) U.S. Cl.
   CPC ............... *A24D 1/20* (2020.01); *A24F 40/46* (2020.01); *A61M 11/042* (2014.02); *A61M 15/06* (2013.01); *A24F 40/20* (2020.01)

(56) References Cited

U.S. PATENT DOCUMENTS

| | | |
|---|---|---|
| 239,776 A | 4/1881 | Henley |
| D22,270 S | 3/1893 | Marshall |
| D27,458 S | 8/1897 | Alexander |
| 844,272 A | 2/1907 | Fate |
| 912,986 A | 2/1909 | Aschenbrenner |
| 1,071,817 A | 9/1913 | Stanley |
| 1,771,366 A | 7/1930 | Wyss et al. |
| 1,886,391 A | 11/1932 | Henri et al. |
| 1,927,956 A | 9/1933 | Samuel et al. |
| 2,104,266 A | 1/1938 | McCormick |
| 2,371,557 A | 3/1945 | Sullivan |
| 3,225,954 A | 12/1965 | Herrick et al. |
| 3,265,236 A | 8/1966 | Norman et al. |
| 3,804,100 A | 4/1974 | Fariello |
| 3,805,806 A | 4/1974 | Grihalva |
| 3,889,690 A | 6/1975 | Guarnieri |
| D239,776 S | 5/1976 | Kenjiro |
| 4,171,000 A | 10/1979 | Uhle |
| 4,214,658 A | 7/1980 | Crow |
| 4,303,083 A | 12/1981 | Burruss, Jr. |
| 4,474,191 A | 10/1984 | Steiner |
| 4,588,976 A | 5/1986 | Jaselli |
| D284,506 S | 7/1986 | Gutknecht |
| 4,628,187 A | 12/1986 | Sekiguchi et al. |
| 4,638,820 A | 1/1987 | Roberts et al. |
| 4,675,508 A | 6/1987 | Miyaji et al. |
| 4,735,217 A | 4/1988 | Gerth et al. |
| 4,756,318 A | 7/1988 | Clearman et al. |
| 4,765,347 A | 8/1988 | Sensabaugh, Jr. et al. |
| D303,766 S | 10/1989 | Delbanco |
| 4,907,606 A | 3/1990 | Lilja et al. |
| 4,922,901 A | 5/1990 | Brooks et al. |
| 4,945,929 A | 8/1990 | Egilmex |
| 4,945,931 A | 8/1990 | Gori |
| 4,947,874 A | 8/1990 | Brooks et al. |
| 4,947,875 A | 8/1990 | Brooks et al. |
| 5,040,551 A | 8/1991 | Schlatter et al. |
| 5,060,671 A | 10/1991 | Counts |
| 5,093,894 A | 3/1992 | Deevi et al. |
| 5,095,921 A | 3/1992 | Losee et al. |
| 5,144,962 A | 9/1992 | Counts et al. |
| 5,179,966 A | 1/1993 | Losee et al. |
| 5,190,060 A | 3/1993 | Gerding et al. |
| 5,203,355 A | 4/1993 | Clearman et al. |
| 5,224,498 A | 7/1993 | Deevi et al. |
| 5,247,947 A | 9/1993 | Clearman et al. |
| 5,249,586 A | 10/1993 | Morgan et al. |
| 5,251,688 A | 10/1993 | Schatz |
| 5,261,424 A | 11/1993 | Sprinkel, Jr. |
| 5,269,327 A | 12/1993 | Counts et al. |
| 5,271,980 A | 12/1993 | Bell |
| 5,285,798 A | 2/1994 | Banerjee et al. |
| 5,303,720 A | 4/1994 | Banerjee et al. |
| 5,322,075 A | 6/1994 | Deevi et al. |
| 5,327,915 A | 7/1994 | Porenski et al. |
| 5,331,979 A | 7/1994 | Henley |
| 5,345,951 A | 9/1994 | Serrano et al. |
| 5,353,813 A | 10/1994 | Deevi et al. |
| 5,369,723 A | 11/1994 | Counts et al. |
| 5,388,594 A | 2/1995 | Counts et al. |
| 5,402,803 A | 4/1995 | Takagi |
| 5,408,574 A | 4/1995 | Deevi et al. |
| D360,281 S | 7/1995 | Kim |
| 5,468,936 A | 11/1995 | Deevi et al. |
| 5,505,214 A | 4/1996 | Collins et al. |
| 5,564,442 A | 10/1996 | MacDonald et al. |
| 5,573,140 A | 11/1996 | Satomi et al. |
| 5,613,504 A | 3/1997 | Collins et al. |
| 5,613,505 A * | 3/1997 | Campbell ............... A24F 40/53 131/194 |
| 5,665,262 A | 9/1997 | Hajaligol et al. |
| 5,771,845 A | 6/1998 | Pistien et al. |
| 5,798,154 A | 8/1998 | Bryan |
| 5,865,186 A | 2/1999 | Volsey, II |
| 5,878,752 A | 3/1999 | Adams et al. |
| 6,026,820 A | 2/2000 | Baggett, Jr. et al. |
| D422,113 S | 3/2000 | Higgins et al. |
| 6,037,568 A | 3/2000 | Hatanaka et al. |
| 6,040,560 A | 3/2000 | Fleischhauer et al. |
| D424,236 S | 5/2000 | Reed |
| 6,089,857 A | 7/2000 | Matsuura et al. |
| 6,125,853 A | 10/2000 | Susa et al. |
| 6,155,268 A | 12/2000 | Takeuchi |
| D437,112 S | 2/2001 | Toffoli |
| D446,849 S | 8/2001 | Weinberg |
| 6,315,366 B1 | 11/2001 | Post et al. |
| 6,376,816 B2 | 4/2002 | Cooper et al. |
| 6,868,230 B2 | 3/2005 | Gerhardinger |
| D506,001 S | 6/2005 | Christianson |
| D512,493 S | 12/2005 | Haranaka |
| 6,994,096 B2 | 2/2006 | Rostami et al. |
| D538,222 S | 3/2007 | Curello et al. |
| D558,330 S | 12/2007 | Chang |
| 7,374,063 B2 | 5/2008 | Reid |
| D576,718 S | 9/2008 | Nomi et al. |
| 7,624,739 B2 | 12/2009 | Snaidr et al. |
| D634,417 S | 3/2011 | Abbondanzio et al. |
| D634,832 S | 3/2011 | Abbondanzio et al. |
| 7,913,688 B2 | 3/2011 | Cross et al. |
| D643,732 S | 8/2011 | Cummings et al. |
| 7,988,660 B2 | 8/2011 | Byland et al. |
| D645,757 S | 9/2011 | Milhem et al. |
| 8,061,361 B2 | 11/2011 | Maeder et al. |
| D650,472 S | 12/2011 | Petersen |
| 8,079,371 B2 | 12/2011 | Robinson et al. |
| 8,081,474 B1 | 12/2011 | Zohni et al. |
| D654,160 S | 2/2012 | Yomtov |
| D663,891 S | 7/2012 | Cohen Harel |
| D664,709 S | 7/2012 | Almsberger et al. |
| D665,734 S | 8/2012 | Fitch et al. |
| D674,479 S | 1/2013 | Merchant et al. |
| D677,623 S | 3/2013 | Fitch et al. |
| D677,774 S | 3/2013 | Postma |
| 8,528,780 B2 | 9/2013 | Houghton et al. |
| D695,396 S | 12/2013 | Tani et al. |
| D696,815 S | 12/2013 | Abroff |
| D700,397 S | 2/2014 | Manca et al. |
| 8,678,013 B2 | 3/2014 | Crooks et al. |
| D704,319 S | 5/2014 | Cai |
| 8,757,404 B1 | 6/2014 | Fleckenstein |
| D708,129 S | 7/2014 | Houghton et al. |
| D708,727 S | 7/2014 | Postma |
| 8,807,140 B1 | 8/2014 | Scatterday |
| 8,833,364 B2 | 9/2014 | Buchberger |
| D714,647 S | 10/2014 | Kersten |
| D715,760 S | 10/2014 | Kim et al. |
| D716,267 S | 10/2014 | Kim et al. |
| D728,855 S | 5/2015 | Liu |
| D729,440 S | 5/2015 | Liu |
| D729,445 S | 5/2015 | Leidel |
| D736,455 S | 8/2015 | Liu |
| D740,673 S | 10/2015 | Corradini et al. |
| D743,099 S | 11/2015 | Oglesby |
| D743,889 S | 11/2015 | Lyles et al. |
| D745,404 S | 12/2015 | Julier et al. |
| D746,771 S | 1/2016 | Perez |
| D758,656 S | 6/2016 | Freshwater et al. |
| D759,296 S | 6/2016 | Abroff et al. |
| D760,414 S | 6/2016 | Brown et al. |
| 9,357,803 B2 | 6/2016 | Egoyants et al. |

(56) References Cited

U.S. PATENT DOCUMENTS

| | | |
|---|---|---|
| 9,414,629 B2 | 8/2016 | Egoyants et al. |
| D768,834 S | 10/2016 | Schuller et al. |
| D771,867 S | 11/2016 | Leidel et al. |
| D773,114 S | 11/2016 | Leidel et al. |
| D775,762 S | 1/2017 | Chen |
| 9,554,598 B2 | 1/2017 | Egoyants et al. |
| D778,831 S | 2/2017 | Chen |
| 9,609,894 B2 | 4/2017 | Abramov et al. |
| D787,657 S | 5/2017 | Farone et al. |
| D787,728 S | 5/2017 | Wing et al. |
| D788,364 S | 5/2017 | Chen |
| D807,575 S | 1/2018 | Luo |
| D818,637 S | 5/2018 | Ringel |
| D819,023 S | 5/2018 | Shim |
| 9,980,523 B2 | 5/2018 | Abramov et al. |
| D821,640 S | 6/2018 | Qiu |
| 9,999,256 B2 | 6/2018 | Abramov et al. |
| D828,295 S | 9/2018 | Li |
| D828,622 S | 9/2018 | Chen et al. |
| D828,912 S | 9/2018 | Powell et al. |
| D828,950 S | 9/2018 | Gu |
| D828,953 S | 9/2018 | Chen |
| D833,384 S | 11/2018 | Takayanagi |
| 10,136,679 B1 | 11/2018 | Shotey et al. |
| D835,857 S | 12/2018 | Benacquisto et al. |
| D839,823 S | 2/2019 | Lemelson et al. |
| D842,237 S | 3/2019 | Qiu et al. |
| D842,243 S | 3/2019 | Qiu |
| D843,052 S | 3/2019 | Powell et al. |
| D848,603 S | 5/2019 | Fujino et al. |
| D854,236 S | 7/2019 | Qiu |
| D861,549 S | 10/2019 | Lai |
| D869,086 S | 12/2019 | Pan |
| D870,367 S | 12/2019 | Chung et al. |
| D872,355 S | 1/2020 | Powell et al. |
| D876,214 S | 2/2020 | Yu |
| D881,458 S | 4/2020 | Ouyang |
| D883,197 S | 5/2020 | Doucet |
| D883,563 S | 5/2020 | Pan |
| D884,266 S | 5/2020 | Wang |
| D885,332 S | 5/2020 | Han |
| D885,337 S | 5/2020 | Xu |
| D885,651 S | 5/2020 | Miyamoto |
| D888,326 S | 6/2020 | Qiu |
| D888,329 S | 6/2020 | Qiu |
| D889,740 S | 7/2020 | Beer et al. |
| D891,692 S | 7/2020 | Barbaric et al. |
| D892,124 S | 8/2020 | Shim |
| D893,009 S | 8/2020 | Choi |
| D894,476 S | 8/2020 | Miyamoto |
| D897,596 S | 9/2020 | Huang et al. |
| D898,990 S | 10/2020 | Liu et al. |
| D898,991 S | 10/2020 | Pan |
| 2002/0005207 A1 | 1/2002 | Wrenn et al. |
| 2002/0079309 A1 | 6/2002 | Cox et al. |
| 2003/0049025 A1 | 3/2003 | Neumann et al. |
| 2003/0146224 A1 | 8/2003 | Fujii et al. |
| 2004/0003820 A1 | 1/2004 | Iannuzzi |
| 2004/0025865 A1 | 2/2004 | Nichols et al. |
| 2004/0096204 A1 | 5/2004 | Gerhardinger |
| 2004/0149296 A1 | 8/2004 | Rostami et al. |
| 2004/0149297 A1 | 8/2004 | Sharpe |
| 2004/0149737 A1 | 8/2004 | Sharpe et al. |
| 2005/0063686 A1 | 3/2005 | Whittle et al. |
| 2005/0199610 A1 | 9/2005 | Ptasienski et al. |
| 2005/0211711 A1 | 9/2005 | Reid |
| 2005/0268911 A1 | 12/2005 | Cross et al. |
| 2007/0074734 A1 | 4/2007 | Braunshteyn et al. |
| 2007/0102013 A1 | 5/2007 | Adams et al. |
| 2007/0155255 A1 | 7/2007 | Galauner et al. |
| 2007/0204858 A1 | 9/2007 | Abelbeck |
| 2007/0204868 A1 | 9/2007 | Bollinger et al. |
| 2007/0283972 A1 | 12/2007 | Monsees et al. |
| 2008/0085139 A1 | 4/2008 | Roof |
| 2008/0092912 A1 | 4/2008 | Robinson et al. |
| 2008/0216828 A1 | 9/2008 | Wensley et al. |
| 2008/0233318 A1 | 9/2008 | Coyle |
| 2008/0302374 A1 | 12/2008 | Wengert et al. |
| 2009/0032034 A1 | 2/2009 | Steinberg |
| 2009/0056728 A1 | 3/2009 | Baker |
| 2009/0114737 A1 | 5/2009 | Yu et al. |
| 2009/0126745 A1 | 5/2009 | Hon |
| 2009/0151717 A1 | 6/2009 | Bowen et al. |
| 2009/0260641 A1 | 10/2009 | Monsees et al. |
| 2009/0272379 A1 | 11/2009 | Thorens et al. |
| 2009/0304372 A1 | 12/2009 | Gubler et al. |
| 2010/0126516 A1 | 5/2010 | Yomtov et al. |
| 2010/0200006 A1 | 8/2010 | Robinson et al. |
| 2010/0236561 A1 | 9/2010 | Barnes et al. |
| 2010/0242975 A1 | 9/2010 | Hearn |
| 2010/0300467 A1 | 12/2010 | Kuistila et al. |
| 2011/0094523 A1 | 4/2011 | Thorens et al. |
| 2011/0108025 A1 | 5/2011 | Fink et al. |
| 2011/0126848 A1 | 6/2011 | Zuber et al. |
| 2011/0155153 A1 | 6/2011 | Thorens et al. |
| 2011/0226236 A1 | 9/2011 | Buchberger |
| 2011/0240047 A1 | 10/2011 | Adamic |
| 2011/0264084 A1 | 10/2011 | Reid |
| 2011/0290244 A1 | 12/2011 | Schennum |
| 2012/0006342 A1 | 1/2012 | Rose et al. |
| 2012/0255546 A1 | 10/2012 | Goetz et al. |
| 2012/0260927 A1 | 10/2012 | Liu |
| 2013/0042865 A1 | 2/2013 | Monsees et al. |
| 2013/0081623 A1 | 4/2013 | Buchberger |
| 2013/0255702 A1 | 10/2013 | Griffith, Jr. |
| 2013/0306084 A1 | 11/2013 | Flick |
| 2014/0060554 A1 | 3/2014 | Collett et al. |
| 2014/0069444 A1 | 3/2014 | Cyphert et al. |
| 2014/0182608 A1 | 7/2014 | Egoyants et al. |
| 2014/0182843 A1 | 7/2014 | Vinegar |
| 2014/0196718 A1 | 7/2014 | Li et al. |
| 2014/0202476 A1 | 7/2014 | Egoyants et al. |
| 2014/0216485 A1 | 8/2014 | Egoyants et al. |
| 2014/0270726 A1 | 9/2014 | Egoyants et al. |
| 2014/0283825 A1 | 9/2014 | Buchberger |
| 2014/0299125 A1 | 10/2014 | Buchberger |
| 2014/0305449 A1 | 10/2014 | Plojoux et al. |
| 2014/0326257 A1 | 11/2014 | Jalloul et al. |
| 2014/0334802 A1 | 11/2014 | Dubief |
| 2014/0338680 A1 | 11/2014 | Abramov et al. |
| 2014/0360515 A1 | 12/2014 | Vasiliev et al. |
| 2014/0366898 A1 | 12/2014 | Monsees et al. |
| 2015/0040925 A1 | 2/2015 | Saleem et al. |
| 2015/0053217 A1 | 2/2015 | Steingraber et al. |
| 2015/0059787 A1 | 3/2015 | Qiu |
| 2015/0101606 A1 | 4/2015 | White |
| 2015/0101944 A1 | 4/2015 | Li et al. |
| 2015/0181937 A1 | 7/2015 | Dubief et al. |
| 2015/0189919 A1 | 7/2015 | Liu |
| 2015/0223520 A1 | 8/2015 | Phillips et al. |
| 2015/0245658 A1 | 9/2015 | Worm et al. |
| 2016/0003403 A1 | 1/2016 | Smith |
| 2016/0007652 A1 | 1/2016 | Taluskie et al. |
| 2016/0081395 A1 | 3/2016 | Thorens et al. |
| 2016/0255879 A1 | 9/2016 | Paprocki et al. |
| 2017/0119048 A1 | 5/2017 | Kaufman et al. |
| 2017/0119049 A1 | 5/2017 | Blandino et al. |
| 2017/0119050 A1 | 5/2017 | Blandino et al. |
| 2017/0156406 A1 | 6/2017 | Abramov et al. |
| 2017/0156407 A1 | 6/2017 | Abramov et al. |
| 2017/0164657 A1 | 6/2017 | Batista |
| 2017/0197043 A1 | 7/2017 | Buchberger |
| 2017/0197044 A1 | 7/2017 | Buchberger |
| 2017/0197046 A1 | 7/2017 | Buchberger |
| 2017/0215480 A1 | 8/2017 | Qiu |
| 2017/0231276 A1 | 8/2017 | Mironov et al. |
| 2017/0232211 A1 | 8/2017 | Gallem et al. |
| 2017/0280779 A1 | 10/2017 | Qiu |
| 2017/0360103 A1 | 12/2017 | Li et al. |
| 2018/0168224 A1 | 6/2018 | Naughton et al. |
| 2018/0271151 A1 | 9/2018 | Litten |
| 2018/0271153 A1 | 9/2018 | John et al. |
| 2018/0271171 A1 | 9/2018 | Abramov et al. |
| 2018/0352860 A1 | 12/2018 | Qiu |

(56) References Cited

U.S. PATENT DOCUMENTS

| | | |
|---|---|---|
| 2019/0029326 A1 | 1/2019 | Qiu |
| 2019/0046745 A1 | 2/2019 | Nettenstrom et al. |
| 2019/0150508 A1 | 5/2019 | Thorsen et al. |
| 2019/0159517 A1 | 5/2019 | Ballesteros Gomez et al. |
| 2019/0166918 A1 | 6/2019 | Thorsen et al. |
| 2019/0200678 A1 | 7/2019 | Thorson et al. |
| 2019/0208815 A1 | 7/2019 | Thorsen |
| 2019/0208816 A1 | 7/2019 | Thorsen |
| 2019/0208817 A1 | 7/2019 | Qiu et al. |
| 2019/0246693 A1 | 8/2019 | Nettenstrom et al. |
| 2019/0387799 A1 | 12/2019 | Reevell |
| 2020/0245681 A1 | 8/2020 | An |
| 2020/0345960 A1 | 11/2020 | Begin et al. |

FOREIGN PATENT DOCUMENTS

| | | |
|---|---|---|
| CN | 1045691 A | 10/1990 |
| CN | 1122213 A | 5/1996 |
| CN | 1126425 A | 7/1996 |
| CN | 2246744 Y | 2/1997 |
| CN | 1190335 A | 8/1998 |
| CN | 1196660 A | 10/1998 |
| CN | 1196661 A | 10/1998 |
| CN | 1333657 A | 1/2002 |
| CN | 2598364 Y | 1/2004 |
| CN | 1947462 A | 4/2007 |
| CN | 101044795 A | 9/2007 |
| CN | 101238047 A | 8/2008 |
| CN | 101267749 A | 9/2008 |
| CN | 101277622 A | 10/2008 |
| CN | 201185656 Y | 1/2009 |
| CN | 101557728 A | 10/2009 |
| CN | 201375023 Y | 1/2010 |
| CN | 101925309 A | 12/2010 |
| CN | 201869778 U | 6/2011 |
| CN | 102595943 A | 7/2012 |
| CN | 102753047 A | 10/2012 |
| CN | 103359550 A | 10/2013 |
| CN | 103763953 A | 4/2014 |
| CN | 103763954 A | 4/2014 |
| CN | 103974639 A | 8/2014 |
| CN | 104095291 A | 10/2014 |
| CN | 104768407 A | 7/2015 |
| CN | 304659647 | 6/2018 |
| CN | 304659654 | 6/2018 |
| CN | 304691359 | 6/2018 |
| CN | 304696494 | 6/2018 |
| CN | 304724787 | 7/2018 |
| CN | 304840668 | 10/2018 |
| CN | 108783602 A | 11/2018 |
| CN | 108851242 A | 11/2018 |
| CN | 108873981 A | 11/2018 |
| DE | 29713866 U1 | 10/1997 |
| DE | 19854005 A1 | 5/2000 |
| DE | 19854009 A1 | 5/2000 |
| EM | 0026114260001 | 3/2015 |
| EM | 0027270990001 | 9/2017 |
| EM | 0027270990007 | 9/2017 |
| EP | 0358002 A2 | 3/1990 |
| EP | 0358114 A2 | 3/1990 |
| EP | 0430559 A2 | 6/1991 |
| EP | 0430566 A2 | 6/1991 |
| EP | 438862 | 7/1991 |
| EP | 0488488 A1 | 6/1992 |
| EP | 0503767 A1 | 9/1992 |
| EP | 0603613 A1 | 6/1994 |
| EP | 0703735 A1 | 4/1996 |
| EP | 0845220 A1 | 6/1998 |
| EP | 1618803 A1 | 1/2006 |
| EP | 1736065 A1 | 12/2006 |
| EP | 2022349 A1 | 2/2009 |
| EP | 2110033 A1 | 10/2009 |
| EP | 1947965 B1 | 2/2010 |
| EP | 2316286 A1 | 5/2011 |
| EP | 2327318 A1 | 6/2011 |
| EP | 2340729 A1 | 7/2011 |
| EP | 2340730 A1 | 7/2011 |
| EP | 2394520 A1 | 12/2011 |
| EP | 2520186 A1 | 11/2012 |
| EP | 2797448 A2 | 11/2014 |
| GB | 191000639 A | 12/1910 |
| GB | 191126138 A | 3/1912 |
| GB | 426247 A | 3/1935 |
| JP | S62501050 A | 4/1987 |
| JP | S63127399 U | 8/1988 |
| JP | H03192677 A | 8/1991 |
| JP | H03232481 A | 10/1991 |
| JP | H05212100 A | 8/1993 |
| JP | H0590161 U | 12/1993 |
| JP | H06189861 A | 7/1994 |
| JP | H06315366 A | 11/1994 |
| JP | H08942 U | 6/1996 |
| JP | H09107943 A | 4/1997 |
| JP | H1189551 A | 4/1999 |
| JP | H11125390 A | 5/1999 |
| JP | H11169157 A | 6/1999 |
| JP | 2001521123 A | 11/2001 |
| JP | 2003527127 A | 9/2003 |
| JP | 2005036897 A | 2/2005 |
| JP | 2005106350 A | 4/2005 |
| JP | 2005300005 A | 10/2005 |
| JP | 2006501871 A | 1/2006 |
| JP | 2008249003 A | 10/2008 |
| JP | 2009509521 A | 3/2009 |
| JP | 2009537120 A | 10/2009 |
| JP | 2010506594 A | 3/2010 |
| JP | 2010178730 A | 8/2010 |
| JP | 2010213579 A | 9/2010 |
| JP | 2011058538 A | 3/2011 |
| JP | 2011509667 A | 3/2011 |
| JP | 2013509160 A | 3/2013 |
| JP | 5193668 B2 | 5/2013 |
| JP | 2014519586 A | 8/2014 |
| JP | 2014524313 A | 9/2014 |
| JP | 2014525251 A | 9/2014 |
| JP | 2014533513 A | 12/2014 |
| JP | 2015513922 A | 5/2015 |
| JP | 2015521847 A | 8/2015 |
| KR | 0178388 B1 | 2/1999 |
| KR | 19990081973 A | 11/1999 |
| KR | 20010089445 A | 10/2001 |
| KR | 100495099 B1 | 11/2005 |
| KR | 100636287 B1 | 10/2006 |
| KR | 100757450 B1 | 9/2007 |
| KR | 20080060218 A | 7/2008 |
| KR | 20100135865 A | 12/2010 |
| KR | 20120104533 A | 9/2012 |
| KR | 20140070588 A | 6/2014 |
| KR | 20150143877 A | 12/2015 |
| KR | 20180124739 A | 11/2018 |
| RU | 2600092 C2 | 10/2016 |
| UZ | 2238 C | 12/2002 |
| WO | WO-8602528 A1 | 5/1986 |
| WO | WO-9219081 A1 | 10/1992 |
| WO | WO-9406314 A1 | 3/1994 |
| WO | WO-9418860 A1 | 9/1994 |
| WO | WO-9632854 A2 | 10/1996 |
| WO | WO-9741744 A1 | 11/1997 |
| WO | WO-9748295 A1 | 12/1997 |
| WO | WO-9823171 A1 | 6/1998 |
| WO | WO-9920939 A1 | 4/1999 |
| WO | WO-0027232 A1 | 5/2000 |
| WO | WO-0167819 A1 | 9/2001 |
| WO | WO-0170054 A1 | 9/2001 |
| WO | WO-03012565 A1 | 2/2003 |
| WO | WO-03037412 A2 | 5/2003 |
| WO | WO-03059413 A2 | 7/2003 |
| WO | WO-03070031 A1 | 8/2003 |
| WO | WO-03103387 A2 | 12/2003 |
| WO | WO-2007012007 A2 | 1/2007 |
| WO | WO-2007017482 A1 | 2/2007 |
| WO | WO-2007039794 A2 | 4/2007 |
| WO | WO-2007131450 A1 | 11/2007 |
| WO | WO-2008108889 A1 | 9/2008 |

(56) References Cited

FOREIGN PATENT DOCUMENTS

| | | |
|---|---|---|
| WO | WO-2008121610 A1 | 10/2008 |
| WO | WO-2009001082 A1 | 12/2008 |
| WO | WO-2009022232 A2 | 2/2009 |
| WO | WO-2009092862 A1 | 7/2009 |
| WO | WO-2010047389 A1 | 4/2010 |
| WO | WO-2010073018 A1 | 7/2010 |
| WO | WO-2010107613 A1 | 9/2010 |
| WO | WO-2010118644 A1 | 10/2010 |
| WO | WO-2010133342 A1 | 11/2010 |
| WO | WO-2011050964 A1 | 5/2011 |
| WO | WO-2011063970 A1 | 6/2011 |
| WO | WO-2011068020 A1 | 6/2011 |
| WO | WO-2011079932 A1 | 7/2011 |
| WO | WO-2013022936 A1 | 2/2013 |
| WO | WO-2013025921 A1 | 2/2013 |
| WO | WO-2013034454 A1 | 3/2013 |
| WO | WO-2013034458 A1 | 3/2013 |
| WO | WO-2013034459 A1 | 3/2013 |
| WO | WO-2013034460 A1 | 3/2013 |
| WO | WO-2013076098 A2 | 5/2013 |
| WO | WO-2013098395 A1 | 7/2013 |
| WO | WO-2013098396 A2 | 7/2013 |
| WO | WO-2013098397 A2 | 7/2013 |
| WO | WO 2013131764 | 9/2013 |
| WO | WO-2013160112 A2 | 10/2013 |
| WO | WO-2014102092 A1 | 7/2014 |
| WO | WO-2014201432 A1 | 12/2014 |
| WO | WO 2015062983 | 5/2015 |
| WO | WO 2015071682 | 5/2015 |
| WO | WO-2015091258 A1 | 6/2015 |
| WO | WO-2015166245 A2 | 11/2015 |
| WO | WO-2015177254 A1 | 11/2015 |
| WO | WO 2016005533 | 1/2016 |
| WO | WO-2016012774 A1 | 1/2016 |
| WO | WO-2016207407 A1 | 12/2016 |
| WO | WO-2017194762 A1 | 11/2017 |
| WO | WO-2017194763 A2 | 11/2017 |
| WO | WO-2017194764 A1 | 11/2017 |
| WO | WO-2017194766 A1 | 11/2017 |
| WO | WO-2017194769 A1 | 11/2017 |
| WO | 2018002086 A1 | 1/2018 |
| WO | 2018019855 A1 | 2/2018 |
| WO | WO-2018019786 A1 | 2/2018 |
| WO | 2018190590 A2 | 10/2018 |
| WO | 2019005526 A1 | 1/2019 |
| WO | 2020182772 A1 | 9/2020 |

OTHER PUBLICATIONS

Application and File History for U.S. Appl. No. 16/099,315, filed Nov. 6, 2018, Inventor: Thorsen.
Application and File History for U.S. Appl. No. 13/583,381, filed Dec. 17, 2012, inventor Buchberger.
Application and File History for U.S. Appl. No. 14/127,138, filed Feb. 10, 2014, inventors Egoyants et al.
Application and File History for U.S. Appl. No. 14/127,144, filed Mar. 31, 2014, inventors Egoyants et al.
Application and File History for U.S. Appl. No. 14/127,148, filed Mar. 12, 2014, inventors Egoyants et al.
Application and File History for U.S. Appl. No. 14/127,879, filed May 9, 2014, inventors Egoyants et al.
Application and File History for U.S. Appl. No. 14/343,368, filed Jun. 24, 2014, inventors Abramov et al.
Application and File History for U.S. Appl. No. 14/382,198, filed Aug. 29, 2014, inventors Saleem et al.
Application and Filing Receiptfor U.S. Appl. No. 29/557,914, filed Mar. 14, 2016, 280 pages, inventor(s): Powell et al.
Collier J.G. et al., "10.3 Mechanism of Evaporation and Condensation," Convective Boiling and Condensation, Third Edition, Clarendon Press, 1994, 6 pages.
Concept Group, "Insulon® Thermal Barrier from Concept Group Blocks Heat with Hyper-Deep Vacuum™," Dec. 15, 2011, 1 page.
Davies, et al., "Metallic Foams: Their Production, Properties and Applications," Journal of Materials Science, 1983, vol. 18(7), pp. 1899-1911.
Decision to Grant a Patent dated Nov. 15, 2016 for Japanese Application No. 2015-506185 filed Apr. 11, 2013, 5 pages.
Decision to Grant dated Jan. 18, 2017 for Russian Application No. 2016503074, 4 pages.
English Translation of Office Action dated Dec. 25, 2018 for Korean Application No. 10-2017-7037332, 7 pages.
Examination Report dated Jan. 9, 2019 for Philippines Application No. 1/2016/500805, 6 pages.
Examination Report dated Feb. 21, 2018 for Australian Application No. 2016204192, 7 pages.
First Office Action dated Jun. 15, 2015 and Search Report dated Jun. 2, 2015 for Chinese Application No. 201280029784.X, filed Aug. 24, 2012, 27 pages.
First Office Action dated Dec. 3, 2015 for Chinese Application No. 201380021387.2, filed Apr. 11, 2011, 20 pages.
"Glo E-cigarette", published 2016, retrieved from https://ifworlddesignguide.com/entry/235574-glo onDec. 5, 2020, 4 pages.
U.S. Appl. No. 29/687,461, filed Apr. 12, 2019, 185 pages, inventor(s): Powell et al.
U.S. Appl. No. 29/687,464, filed Apr. 12, 2019, 176 pages, inventor(s): Powell et al.
U.S. Appl. No. 29/687,469, filed Apr. 12, 2019, 147 pages, inventor(s): Powell et al.
U.S. Appl. No. 29/687,471, filed Apr. 12, 2019, 222 pages, inventor(s): Powell et al.
U.S. Design U.S. Appl. No. 29/705,487, filed Sep. 12, 2019 inventor(s): Powell et al.
U.S. Appl. No. 15/737,673, filed Dec. 18, 2017, inventor(s): Thorsen et al.
International Preliminary Report on Patentability for Application No. PCT/EP2017/068804, dated Feb. 7, 2019, 8 pages.
International Preliminary Report on Patentability for Application No. PCT/EP2012/066484, dated Mar. 20, 2014, 7 pages.
International Preliminary Report on Patentability for Application No. PCT/EP2017/061518, dated Aug. 17, 2018, 16 pages.
International Preliminary Report on Patentability for Application No. PCT/EP2017/061519, dated Jul. 25, 2018, 22 pages.
International Preliminary Report on Patentability for Application No. PCT/EP2017/061526, dated Nov. 22, 2018, 10 pages.
International Preliminary Report on Patentability for Application No. PCT/EP2017/068675, dated Nov. 29, 2018, 7 pages.
International Preliminary Report on Patentability for International Application No. PCT/EP2017/061520, dated Jul. 17, 2018, 11 pages.
International Preliminary Report on Patentability for International Application No. PCT/EP2017/061523, dated Jul. 23, 2018, 14 pages.
International Preliminary Report on Patentability for Application No. PCT/EP2012/066486, dated Oct. 22, 2013, 10 pages.
International Preliminary Report on Patentability for Application No. PCT/EP2012/066523, dated Nov. 4, 2013, 9 pages.
International Preliminary Report on Patentability for Application No. PCT/EP2012/066524, dated Oct. 17, 2013, 11 pages.
International Search Report and Written Opinion for Application No. PCT/EP2013/057539, dated Feb. 11, 2014, 16 pages.
International Search Report and Written Opinion for Application No. PCT/EP2017/061519, dated Dec. 15, 2017, 22 pages.
International Search Report and Written Opinion for Application No. PCT/EP2017/061520, dated Sep. 11, 2017, 13 pages.
International Search Report and Written Opinion for Application No. PCT/EP2017/061523, dated Sep. 11, 2017, 13 pages.
International Search Report and Written Opinion for Application No. PCT/EP2017/068675, dated Nov. 9, 2017, 15 pages.
International Search Report and Written Opinion for Application No. PCT/EP2012/066484, dated Jan. 9, 2013, 9 pages.
International Search Report and Written Opinion for Application No. PCT/EP2012/066486, dated Jan. 14, 2013, 8 pages.
International Search Report and Written Opinion for Application No. PCT/EP2012/066523, dated Jan. 9, 2013, 9 pages.

(56) References Cited

OTHER PUBLICATIONS

International Search Report and Written Opinion for Application No. PCT/EP2012/066524, dated Jan. 9, 2013, 8 pages.
International Search Report and Written Opinion for Application No. PCT/EP2012/066525, dated Jan. 9, 2013, 10 pages.
International Search Report and Written Opinion for Application No. PCT/EP2012/066485, dated Dec. 10, 2012, 10 pages.
International Search Report and Written Opinion for Application No. PCT/AT2011/000123, dated Jul. 18, 2011, 8 pages.
International Search Report for Application No. PCT/EP2016/064756, dated Oct. 5, 2016, 2 pages.
International Search Report for Application No. PCT/EP2017/061518, dated Aug. 1, 2017, 4 pages.
International Search Report for Application No. PCT/EP2017/061526, dated Aug. 2, 2017, 4 pages.
National Plastic Heater, Sensor and Control Inc., "Kapton (Polyimide) Flexible Heaters," 2011, retrieved from https://www.kapton-silicone-flexible-heaters.com/products/kapton_polyimide_flexible_heaters.html on Feb. 23, 2018, 2 pages.
Notice of Opposition dated Mar. 7, 2017 for European Application No. 12750770.5, 22 pages.
Notice of Reasons for Refusal dated Nov. 20, 2018 for Japanese Application No. 2017-567106, 6 pages.
Office Action dated Jul. 8, 2016 for Chinese Application No. 201380021387.2, filed Apr. 11, 2011, 12 pages.
Office Action dated Sep. 25, 2018 for European Application No. 12750765.5 filed Aug. 24, 2012, 22 pages.
Office Action dated Sep. 26, 2018 for European Application No. 12750765.5 filed Aug. 24, 2012, 67 pages.
Office Action dated Sep. 29, 2015 for Japanese Application No. 2015-506185 filed Apr. 11, 2013, 5 pages.
Office Action dated Mar. 31, 2015 for Japanese Application No. 2014-519585 filed Aug. 24, 2012, 8 pages.
Office Action dated Apr. 7, 2015 for Japanese Application No. 2014-519586 filed Aug. 24, 2012, 10 pages.
Office Action and Search Report dated Apr. 27, 2015 for Chinese Application No. 201280030681.5, filed Aug. 24, 2012, 25 pages.
Office Action dated Sep. 4, 2020 for Korean Application No. 10-2019-7002616, 9 pages.
Office Action dated Sep. 6, 2017 for Korean Application No. 10-2017-7017425, 9 pages.
Office Action dated Sep. 6, 2017 for Korean Application No. 10-2017-7017430, 9 pages.
Office Action dated Jan. 10, 2020 for Indian Application No. 201847042184, 5 pages.
Office Action dated Mar. 10, 2020 for Japanese Application No. 2018-555932, 10 pages.
Office Action dated Aug. 17, 2016 for Korean Application No. 10-2014-7032958, 13 pages.
Office Action dated Aug. 17, 2020 for Chinese Application No. 201780028992.0, 13 pages.
Office Action dated Feb. 18, 2020 for Japanese Application No. 2018-559712, 6 pages.
Office Action dated Jul. 20, 2017 for Chilean Application No. 2014-002840, 7 pages.
Office Action dated Apr. 24, 2019 for Chinese Application No. 201710413187.1, 16 pages.
Office Action dated Feb. 25, 2020 for Japanese Application No. 2018-554526, 12 pages.
Office Action dated Dec. 26, 2017 for Chinese Application No. 201480059966.0, 29 pages.
Office Action dated Jul. 27, 2018 for Korean Application No. 10-2013-7033866, 22 pages.
Office Action dated Jun. 27, 2017 for Japanese Application No. 2016-527295, 8 pages.
Office Action dated Aug. 28, 2019 for Indian Application No. 201647014549, 6 pages.
Office Action dated Jan. 28, 2020 for Japanese Application No. 2018-551932, 6 pages.
Office Action dated Jul. 28, 2017 for Korean Application No. 10-2016-7010831, 11 pages.
Office Action dated Jun. 28, 2019 for Russian Application No. 2018139838, 5 pages.
Office Action dated Jan. 6, 2020 for Chinese Application No. 201680037678.4, 10 pages.
Office Action dated Feb. 25, 2020 for Japanese Application No. 2018-554501, 12 pages.
Office Action dated Oct. 15, 2019 for Russian Application No. 2019102040, 8 pages.
Office Action dated Mar. 17, 2020 for Japanese Application No. 2019503268, 5 pages.
Office Action dated Oct. 20, 2020 for Japanese Application No. 2019503268, 2 pages.
Office Action dated Sep. 24, 2020 for Chinese Application No. 201780045799.8, 13 pages.
Patio Kits Direct, "Insulated Roof Panels," DIY Alumawood Patio Cover Kits, dated Sep. 20, 2018, as available at https://www.patiokitsdirect.com/about-insulation, 2 pages.
Search Report dated Mar. 24, 2015 for Chinese Application No. 201280029767.6 filed Aug. 24, 2012, 6 pages.
Search Report dated Dec. 25, 2019 for Chinese Application No. 201680037678.4, 2 pages.
Second Office Action dated Jan. 16, 2017 for Chinese Application No. 201380048636.7, 24 pages.
Translation of Office Action dated Mar. 25, 2019 for Chinese Application No. 201610804046.8, 17 pages.
Uranaka T., et al., "British American Tobacco to Test Tobacco E-cigarette in Japan," Nov. 8, 2016, Retrieved from http://www.reuters.com/article/us-brit-am-tobacco-ecigarettes-idUSKBN1330AG on Apr. 7, 2017, 4 pages.
Warrier M., et al., "Effect of the Porous Structure of Graphite on Atomic Hydrogen Diffusion and Inventory," Nucl. Fusion, vol. 47, 2007, pp. 1656-1663.
Written Opinion for Application No. PCT/EP2012/066485, dated Oct. 15, 2013, 6 pages.
Written Opinion for Application No. PCT/EP2017/061526, dated Aug. 2, 2017, 8 pages.
Written Opinion and ISR for Application No. PCT/EP2017/068804, dated Oct. 27, 2017, 6 pages.
Application and File History for U.S. Appl. No. 16/320,598, filed Jan. 25, 2019, inventors Ballesteros Gomez et al.
Extended European Search Report for European Patent Application No. 21162875.5, dated Oct. 6, 2021, 15 pages.
Notice of Reasons for Refusal received for Japanese Patent Application No. 2021007415, dated Mar. 22, 2022, 7 pages (4 pages of English Translation and 3 pages of Official Copy).
Office Action for Korean Patent Application No. 10-2021-7023737, dated May 11, 2022, 5 pages (English Translation Only).
Office Action For Korean Patent Application No. 10-2021-7023737, dated Oct. 20, 2021, 4 pages (English Translation Only).
Office Action received for Australian Patent Application No. 2020236478, dated Jun. 21, 2022, 3 pages.

\* cited by examiner

METHOD OF GENERATING AEROSOL

PRIORITY CLAIM

The present application a divisional of U.S. application Ser. No. 16/320,598 filed Jan. 25, 2019, which is a National Phase entry of PCT Application No. PCT/EP2017/068804, filed Jul. 25, 2017, which claims priority from GB Patent Application No. 1612945.4, filed Jul. 26, 2016, which is hereby fully incorporated herein by reference.

TECHNICAL FIELD

The present invention relates to an aerosol-generating device, and a method of generating aerosol using the aerosol-generating device.

BACKGROUND

Articles such as cigarettes, cigars and the like burn tobacco during use to create tobacco smoke. Attempts have been made to provide alternatives to these types of articles, which burn tobacco, by creating products that release compounds without burning. Apparatus is known that heats smokable material to volatilise at least one component of the smokable material, typically to form an aerosol which can be inhaled, without burning or combusting the smokable material. Such apparatus is sometimes described as a "heat-not-burn" apparatus or a "tobacco heating product" (THP) or "tobacco heating device" or similar. Various different arrangements for volatilising at least one component of the smokable material are known.

The material may be for example tobacco or other non-tobacco products or a combination, such as a blended mix, which may or may not contain nicotine.

SUMMARY

At its most general, the present invention provides a method of generating aerosol from an aerosol-generating substrate using an aerosol-generating device, wherein portions of the aerosol-generating substrate have different temperature profiles.

According to a particular embodiment of the present invention, there is provided:
1) a method of generating aerosol from an aerosol-generating substrate using an aerosol-generating device with at least one heat source disposed to heat, but not burn, the aerosol-generating substrate in use;
   wherein the aerosol-generating substrate comprises first and second portions having substantially the same composition, and/or wherein the aerosol-generating substrate comprises first and second portions and there is no physical separation between the portions;
   the method comprising the steps of:
heating the aerosol-generating substrate in the aerosol-generating device, so that a temperature profile of the first portion of the aerosol-generating substrate during heating is different from a temperature profile of the second portion of the aerosol-generating substrate.

By controlling the temperature of the first and second portions over time such that the temperature profiles of the portions are different, it is possible to control the puff profile of the aerosol during use.
2) A method according to 1), wherein the heating has a duration of at least 2 minutes, and the temperature of each of the first and second portions of the aerosol-generating substrate is greater than 100° C. for at least half the duration of the heating.
3) A method according to any of 1) to 2), wherein the device comprises:
   a first heat source disposed to heat, but not burn, the first portion of the aerosol-generating substrate in use; and
   a second heat source disposed to heat, but not burn, the second portion of the aerosol-generating substrate in use.

By using a plurality of heat sources, it is possible to accurately control the temperature profiles of the respective portions of aerosol-generating substrate by controlling the heating profiles of each of the heat sources.
4) A method according to 3), in which during said heating, the heating profile of the first heat source is different from the heating profile of the second heat source.

The use of a plurality of heat sources with different heating profiles provides different temperature profiles in the respective portions of the substrate.
5) A method according to any of 3) to 4), wherein the first and second heat sources are independently controllable.
6) A method according to any of 3) to 5), wherein the first heat source begins to heat the aerosol-generating substrate before the second heat source.

Staggering the heating in this way may allow for both fast aerosol production and longevity of use.

Fast aerosol production and longevity of use may also be provided by a method wherein the first heat source provides heat to the aerosol-generating substrate at a different rate from the second heat source.
7) A method according to any of 1) to 6), wherein the device has a mouth end and a distal end, and the first portion of the aerosol-generating substrate is disposed closer to the mouth end of the device than the second aerosol-generating substrate.
8) A method according to any of 1) to 7), wherein once the at least one or each heat source has begun to heat the aerosol-generating substrate, said heat source continues to heat the aerosol-generating substrate until the end of a period of time corresponding to a single session.
9) A method according to any of 1) to 8), wherein the device comprises a thermally insulative component disposed between the at least one heat source and the aerosol-generating substrate in use, wherein the configuration of the thermally insulative material is different for the first and second portions of the aerosol-generating substrate.

This method allows different temperature profiles to be imparted on the various portions of the substrate with the use of one heat source.
10) A method according to 9), wherein the first and second portions of the aerosol-generating substrate are heated by a single heat source.

In a particular embodiment of this method, the temperature of the first portion begins to rise before the second portion of the aerosol-generating substrate. This may be particularly advantageous as it may allow for both fast aerosol production and longevity of use.
11) A method according to any of 1) to 10), wherein the aerosol-generating substrate comprises a tobacco component.
12) A method according to any of 1) to 11), wherein the aerosol-generating device is a Tobacco Heating Product.
13) A method according to any of 1) to 12), wherein the aerosol-generating substrate comprises a tobacco component in an amount of from 60 to 90% by weight of the aerosol-generating substrate, a filler in an amount of 0 to 20% by weight of the aerosol-generating substrate, and an aerosol generating agent in an amount of from 10 to 20% by weight of the tobacco composition.

14) A method according to any of 1) to 13), wherein the temperature of the at least one heat source or each of the heat sources does not exceed 240° C.

15) A method according to any of 1) to 14), wherein the device comprises a power source for providing power to the at least one heat source.

16) A method according to any of 1) to 15), wherein the at least one heat source is a thin film heater.

17) A method according to any of 1) to 16), wherein the aerosol-generating device provides a substantially constant puff profile from the aerosol-generating substrate.

18) An aerosol-generating device comprising:
   a heating chamber having first and second heating zones disposed to heat, but not burn, an aerosol-generating substrate in use;
   where the device is configured such that in use the heating profile of the first heating zone is different from the heating profile of the second heating zone.

19) A device according to 18), wherein the device further comprises an aerosol-generating substrate having first and second portions disposed within the heating chamber, wherein said first and second heating zones are disposed to heat, but not burn, first and second portions of the aerosol-generating substrate respectively.

Further features and advantages of the invention will become apparent from the following description of preferred embodiments of the invention, given by way of example only, which is made with reference to the accompanying drawings.

DETAILED DESCRIPTION

Figure 1:
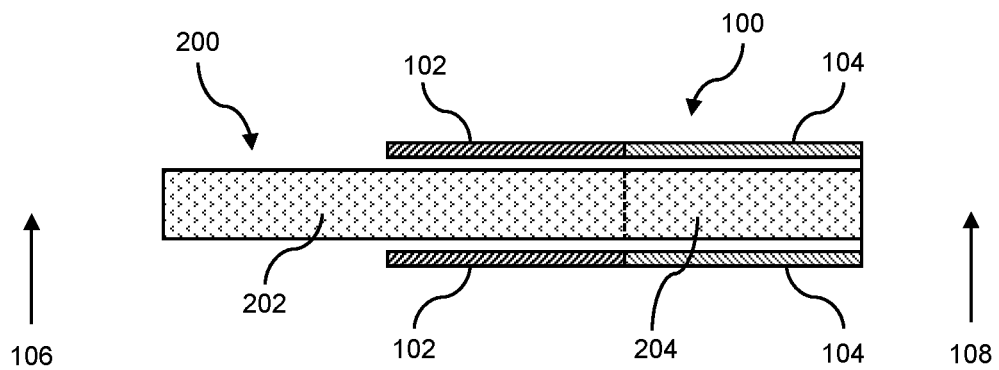
FIG. 1 is a schematic diagram of an aerosol-generating device according to an embodiment of the present invention, showing a cross-section of the heating chamber with the aerosol-generating substrate disposed therein.

As used herein, "the" may be used to mean "the" or "the or each" as appropriate. In particular, features described in relation to "the at least one heat source" may be applicable to the first, second or further heat sources where present. Further, features described in respect of a "first" or "second" heat source may be equally applicable to the other heat source in different embodiments.

As used herein, the term "aerosol-generating substrate" refers to material that provides volatilised components upon heating in the form of an aerosol. In some embodiments, the aerosol-generating substrate may comprise a tobacco component, wherein tobacco component is any material comprising tobacco or derivatives thereof. The tobacco component may comprise one or more of ground tobacco, tobacco fibre, cut tobacco, extruded tobacco, tobacco stem, reconstituted tobacco and/or tobacco extract. In some embodiments, the aerosol-generating substrate may comprise a tobacco substitute.

An aerosol-generating device refers to any apparatus which generates an aerosol from an aerosol-generating substrate when in use. In particular, apparatus is known that heats an aerosol-generating substrate to form an aerosol which can be inhaled, without burning or combusting the aerosol-generating substrate. Such apparatus is sometimes described as a "heat-not-burn" apparatus or a "tobacco heating product" or "tobacco heating device" or similar.

Similarly, there are also so-called e-cigarette devices, which typically vaporise an aerosol-generating substrate in the form of a liquid, which may or may not contain nicotine. However, the aerosol-generating device as contemplated herein provides an aerosol or vapour by heating an aerosol-generating substrate in the form of a solid. In a particular embodiment, the aerosol-generating device is a tobacco heating product.

An aerosol-generating device for use in the present invention is typically generally elongate. The device has a first or proximal or mouth end and a second or distal end. In use, the user will inhale the formed aerosol from the mouth end of the aerosol-generating device. The mouth end may be an open end.

The solid aerosol-generating substrate may be any shape suitable for use with an aerosol-generating device. The aerosol-generating substrate may be in the form of or provided as part of a cartridge or cassette or rod which can be inserted into the apparatus. In some embodiments, the aerosol-generating substrate is an elongate rod. In particular, the aerosol-generating substrate may be an elongate rod comprising a tobacco component.

The aerosol-generating substrate may comprise a plurality of portions. A "portion" as used in this context refers to a particular spatial part of the aerosol-generating substrate. There may be physical separation between these portions, or, more usually, there may be no physical separation between these portions: that is, a portion of the aerosol-generating substrate may simply refer to a particular spatial part of a unitary, whole substrate. Portions of the aerosol-generating substrate need not be the same size as each other.

The aerosol-generating substrate may comprise two portions: a first and second portion. In one embodiment, the aerosol-generating substrate comprises first and second portions, wherein the aerosol-generating substrate is a unitary body. That is, the aerosol-generating substrate is a continuous body where there is no physical separation between the first and second portions, which may or may not have the same composition throughout.

The first and second portions of the aerosol-generating substrate may have substantially the same composition. In some embodiments, the aerosol-generating substrate may consist of a first and second portion, wherein the first and second portions have substantially the same composition, such that the aerosol-generating substrate consists of that composition. Where there is a plurality of portions of aerosol-generating substrate, any number of the substrate portions may have substantially the same composition. In a particular example, all of the portions of the substrate have substantially the same composition. In one embodiment, the aerosol-generating substrate is a unitary, continuous body and there is no physical separation between the first and second portions, and the first and second portions have substantially the same composition.

In another embodiment, the first and second portions of the aerosol-generating substrate comprise different components; that is, they do not have substantially the same composition. In particular, in embodiments wherein the aerosol-generating substrate is a unitary, continuous body and there is no physical separation between the first and second portions, the first and second portions may comprise different components.

The aerosol-generating substrate may comprise more than two portions. For example, the aerosol-generating substrate may comprise three, four, five, or more than five portions.

In a particular embodiment, the aerosol-generating substrate may comprise one or more tobacco components, filler components, binders and aerosol generating agents.

The filler component may be any suitable inorganic filler material. Suitable inorganic filler materials include, but are not limited to: calcium carbonate (i.e. chalk), perlite, vermiculite, diatomaceous earth, colloidal silica, magnesium oxide, magnesium sulphate, magnesium carbonate, and suitable inorganic sorbents, such as molecular sieves. Calcium carbonate is particularly suitable. In some cases, the filler comprises an organic material such as wood pulp, cellulose and cellulose derivatives.

The binder may be any suitable binder. In some embodiments, the binder comprises one or more of an alginate, celluloses or modified celluloses, polysaccharides, starches or modified starches, and natural gums.

Suitable binders include, but are not limited to: alginate salts comprising any suitable cation, such as sodium alginate, calcium alginate, and potassium alginate; celluloses or modified celluloses, such as hydroxypropyl cellulose and carboxymethylcellulose; starches or modified starches; polysaccharides such as pectin salts comprising any suitable cation, such as sodium, potassium, calcium or magnesium pectate; xanthan gum, guar gum, and any other suitable natural gums.

A binder may be included in the aerosol-generating substrate in any suitable quantity and concentration.

The "aerosol generating agent" is an agent that promotes the generation of an aerosol. An aerosol generating agent may promote the generation of an aerosol by promoting an initial vaporisation and/or the condensation of a gas to an inhalable solid and/or liquid aerosol. In some embodiments, an aerosol generating agent may improve the delivery of flavour from the aerosol-generating substrate.

In general, any suitable aerosol generating agent or agents may be included in the aerosol-generating substrate of the invention. Suitable aerosol generating agents include, but are not limited to: a polyol such as sorbitol, glycerol, and glycols like propylene glycol or triethylene glycol; a non-polyol such as monohydric alcohols, high boiling point hydrocarbons, acids such as lactic acid, glycerol derivatives, esters such as diacetin, triacetin, triethylene glycol diacetate, triethyl citrate or myristates including ethyl myristate and isopropyl myristate and aliphatic carboxylic acid esters such as methyl stearate, dimethyl dodecanedioate and dimethyl tetradecanedioate.

In a particular embodiment, the aerosol-generating substrate comprises a tobacco component in an amount of from 60 to 90% by weight of the tobacco composition, a filler component in an amount of 0 to 20% by weight of the tobacco composition, and an aerosol generating agent in an amount of from 10 to 20% by weight of the tobacco composition. The tobacco component may comprise paper reconstituted tobacco in an amount of from 70 to 100% by weight of the tobacco component.

The aerosol-generating device comprises at least one heat source disposed to heat, but not burn, the aerosol-generating substrate in use. In use, the at least one heat source has a heating profile. As used herein, "heating profile" refers to the variation of heat energy emitted from a heat source over time. The heat source is used to provide heat to the aerosol-generating substrate, to generate an aerosol. The heating of the aerosol-generating substrate by the heat source gives rise to the temperature profile of the aerosol-generating substrate. As used herein, "temperature profile" refers to the variation of temperature of a material over time. It follows that the temperature profile of the aerosol-generating substrate derives from the heating profile of the heat source and the insulative property of any intervening space between heat source and substrate (including when that space is filled with material or other components).

For the avoidance of doubt, variation in the temperature of a substrate, and therefore the temperature profile of the substrate, is dependent upon the heat received by the substrate (whether from a heat source in a device or otherwise). It is a product of the heat energy received by the substrate, and the heat capacity of the substrate. It follows that the composition of a substrate may affect its ability to absorb heat energy; that is, the heat capacity of the substrate may vary with composition, thereby affecting the temperature profile of the substrate (more heat energy may be required to change the temperature of the substrate). It also depends on the effectiveness of thermal conduction from a heat source to the substrate: the further a substrate is from the heat source through air, or the more insulation there is between the substrate and a heat source, the more heat energy must be generated by the heat source to change the temperature of the substrate.

Conversely, the heating profile of a heat source is a result of variation of energy generated by the heat source over time. It is not dependent on the composition or configuration of the heat source. Rather, it is an absolute measure of the amount of energy generated from a heat source, which in turn may be experienced by a substrate. This energy experienced may elicit a change in temperature in the substrate, thereby affecting the temperature profile of the substrate. Nevertheless, although it is possible to define the heating profile of a heat source with reference to the output of heat energy over time, it may be appropriate to describe a heating profile with reference to the temperature as measured at the heat source over time.

As used herein, "puff" refers to a single inhalation by the user of the aerosol generated by the aerosol-generating device.

"Operating temperature" as used herein in relation to a portion of an aerosol-generating substrate refers to any temperature of the portion which lies within a temperature range that is sufficient for a desired amount of aerosol to be generated from that portion.

"Operating temperature" as used herein in relation to a heat source refers to any temperature of the heat source which lies within a temperature range that is sufficient to generate a desired amount of aerosol from the aerosol-generating substrate without burning the substrate. An exemplary range of operating temperatures for the heat source according to the present invention might be from 150° C. to 250° C.

"Operating energy output" as used herein refers to any magnitude of heat energy emission from a heat source which lies within a range of magnitudes of heat energy that is sufficient to start generating a desired amount of aerosol from the aerosol-generating substrate without burning the substrate.

The method as described herein is intended to reflect a single session of use, that is, a single period of use of the aerosol-generating device by a user inhaling a generated aerosol, until the aerosol-generating substrate is depleted (the point at which the total particulate matter yield (mg) in each puff would be deemed unacceptably low by a user). The session will have a duration of a plurality of puffs. Said session may have a duration of from 2 to 5 minutes, or from 3 to 4.5 minutes, or 3.5 to 4.5 minutes, or suitably 4 minutes. A session is initiated by the user actuating a button or switch on the device, causing at least one heat source to begin emitting heat energy.

The temperature of each of the portions of aerosol-generating substrate is preferably an elevated temperature for a sustained period during a session. As used herein, "elevated temperature" refers to a temperature higher than 50° C., or higher than 100° C., or higher than 150° C. As used herein "sustained period" refers to a period of time with a duration of a plurality of puffs, which is equal to or less than the duration of the session. For example, a sustained period may be a period of time greater than 30 seconds, or 50 seconds, or 100 seconds, or 150 seconds, or 200 seconds. A sustained period may also be defined in reference to puffs: a sustained period may be a period of time greater than 2, or 5, or 8, or 10 puffs. In particular, the temperature of each portion of the aerosol-generating substrate is preferably an elevated temperature for a sustained period with a duration of at least 25%, 50%, or 75% of the session. In a further embodiment, once a portion of the aerosol-generating substrate is an elevated temperature in the session, it remains at an elevated temperature for the rest of the session.

In some embodiments, the temperature profiles of the portions of aerosol-generating substrate differ in rate of change in temperature. That is, the temperatures of the portions may begin to rise at the same time and reach substantially the same temperature, but reach substantially the same temperature at different points in time. For example, the temperatures of both the first and the second portions of the aerosol-generating substrate may begin to rise at the start of the session, but the first portion may reach an operating temperature relatively quickly, and the second portion may reach such a temperature relatively slowly, after the first portion. That is, the magnitude of the change in temperature over time may be greater for the first portion than the second over a part of the session.

Configuring the first portion of the aerosol-generating substrate to reach an operating temperature rapidly and the second portion to reach an operating temperature more gradually may mean that aerosol is provided to the user quickly, whilst also maintaining longevity of use. As aerosol begins to be generated from the first portion of the aerosol-generating substrate, constituents start to deplete from that portion of the substrate. Gradually increasing the temperature of the second portion allows the introduction of further aerosol to maintain a steady delivery of aerosol to the user.

In other embodiments, the temperature profiles of the portions of aerosol-generating substrate may differ in target temperature. That is, the portions may reach a target temperature at approximately the same time and/or at approximately the same rate, but the target temperatures of the portions are not the same. For example, the temperatures of both the first and the second portions of the aerosol-generating substrate may begin to rise at the same rate at the start of the session, but the first portion of the aerosol-generating substrate may rise to an operating temperature, and the second portion may rise to a temperature which is lower than the temperature of the first portion. In one embodiment, the second portion rises to a temperature which is below operating temperature. In another embodiment, the second portion rises to an operating temperature. In a particular embodiment, in the first part of the session, the first portion reaches an operating temperature, but the second portion reaches an elevated temperature which is below operating temperature.

In further embodiments, the temperature profiles of the portions of aerosol-generating substrate may differ in both the rate of change of temperature and target temperature. For example, the temperature of the first portion may rise to an operating temperature relatively quickly, and the second portion may rise to an elevated temperature which is lower than the temperature of the first portion relatively slowly (the magnitude of the change in temperature over time in the first portion is smaller than that of the first portion for a part of the session).

In yet further embodiments, where the temperature profiles of the portions differ in rate of change of temperature, or differ in target temperature, or both, the temperature profiles of the portions may also differ in start time. For example, the temperature of the portions may also begin to rise at different points in time: the temperature profiles may be "staggered" in time. In one embodiment, the temperature of the first portion may begin to rise at the start of the session, but the temperature of the second portion may begin to rise only once a period of time has elapsed from the start of the session.

There may be a plurality of discernible stages in the temperature profile of a portion of the aerosol-generating substrate. For instance, in a specific example, upon starting the session the first portion of the aerosol-generating substrate may reach a prescribed operating temperature rapidly, and remain at that temperature for a sustained period. In a later part of the session, the temperature of the first portion may fall to a prescribed second temperature, and remain at that temperature for a sustained period. The second temperature is an elevated temperature, and may or may not be an operating temperature. In another specific example, upon starting the session the second portion of the aerosol-generating substrate may rise in temperature to a first temperature very slowly, or not rise at all. In a later part of the session, the temperature of the second portion may rise rapidly to a prescribed second temperature, and remain at that temperature for a sustained period. The second temperature may or may not be an operating temperature. In a still later part of the session, the temperature of the second portion may rise rapidly to a prescribed third temperature, and remain at that temperature for a sustained period. The third temperature is an operating temperature.

In some embodiments, the heat source may be an electrical heating means. In some embodiments, the electrical heating means is an electrically resistive heating element. By "electrically resistive heating element", it is meant that on application of a current to the element, resistance in the element transduces electrical energy into thermal energy which heats the aerosol-generating substrate. The heating element may be in the form of a resistive wire, mesh, coil and/or a plurality of wires. In some embodiments, the heat source may be a thin-film heater.

The heating element may comprise a metal or metal alloy. Metals are excellent conductors of electricity and thermal energy. Suitable metals include but are not limited to: copper, aluminium, platinum, tungsten, gold, silver, and titanium. Suitable metal alloys include but are not limited to: nichrome and stainless steel.

In one embodiment, the heat source may be a material that is heatable by penetration with a varying magnetic field, that is, the aerosol-generating substrate may be heated by induction heating. In this embodiment, the device may comprise an electromagnet and a device for passing a varying electrical current, such as an alternating current, through the electromagnet. When the electromagnet and the heat source are suitably relatively positioned so that the resultant varying magnetic field produced by the electromagnet penetrates the heat source, one or more eddy currents are generated inside the heat source. The heat source has a resistance to the flow of electrical currents, so when such eddy currents are generated in the object, their flow against the electrical resistance of the object causes the object to be heated. An object that is capable of being inductively heated is known as a susceptor. The heat source may be a susceptor.

Using electrical resistance heating systems is advantageous because the rate of heat generation is easier to control, and lower levels of heat are easier to generate, compared with using combustion for heat generation. The use of electrical heating systems therefore allows greater control over the generation of an aerosol from a tobacco composition. Using induction heating systems may also be advantageous—the varying magnetic field magnitude can be easily controlled by controlling the electromagnet. Moreover, as induction heating does not require a physical connection to be provided between the source of the varying magnetic field and the heat source, design freedom and control over the heating profile may be greater, and cost may be lower.

The aerosol-generating device may comprise a power source for providing power to the at least one heat source. Generally, this will be an electrical power source for providing electrical power to the at least one heat source. In an exemplary embodiment, the device further comprises a controller for controlling the supply of electrical power from the electrical power source to the at least one heat source. In such embodiments, it is possible to control the heating profile of the heat source by controlling the power provided to the heat source through time. By controlling the heating profile of the heat source, it is possible to control the temperature profile of the aerosol-generating substrate, thereby controlling the aerosol production of the aerosol-generating device in use.

In order to control the heat output of the heat sources accurately, the device may comprise at least one temperature sensor. The sensor may be disposed near to or in the heat source, or near to or in the aerosol-generating substrate. Suitable temperature sensors include thermocouples, thermopiles or resistance temperature detectors (RTDs, also referred to as resistance thermometers). In a particular embodiment, the device comprises at least one RTD. The temperature data measured by the temperature sensor may be communicated to a controller. Further, it may communicate to the controller when a heat source has reached a prescribed temperature, such that the controller may change the supply of power accordingly.

Where the device comprises at least one electrically resistive heating element, an electrical power source, a controller, and at least one temperature source, the heating profile of the at least one heating element over the session is predefined by the programming of the controller. In a particular embodiment, control of the power supplied to the at least one heating element is not dependent on detection of when a puff occurs. That is, the controller does not activate, deactivate or otherwise significantly change control of a heating element in response to a puff sensor; rather, the heating profiles are predefined according to time points in the session. For example, the controller may be programmed to provide a different amount of power to the at least one heat source after a predefined period of time has elapsed from the initiation of the session by the user, thereby changing the heat output at that time.

By controlling the temperature profiles of the first and second portions of the aerosol-generating substrate such that the temperature profile of the first portion is different from that of the second in use, it is possible to control the so-called "puff profile" during use of the aerosol-generating device. In particular, it is possible to provide a substantially constant puff profile throughout use of the aerosol-generating device. As used herein "puff profile", or "puff per puff profile" refers to the amount of total particulate matter yield (mg) in each puff as the aerosol is consumed by the user.

One method of controlling the temperature profiles of the first and second portions of the aerosol-generating substrate such that the temperature profiles of the portions are different in use is to use an aerosol-generating device comprising two heat sources: a first heat source and a second heat source. Where such a device is used with an aerosol-generating substrate comprising first and second portions, the first heat source is disposed to heat, but not burn, the first portion of the aerosol-generating substrate, and the second heat source is disposed to heat, but not burn, the second portion of the aerosol-generating substrate.

In further embodiments, the device may comprise more than two heat sources. For example, the device may comprise three, four, five, or more than five heat sources. In such examples, the aerosol substrate used with the device will comprise at least three, four, five or more than five portions, as appropriate. It may be that there are a greater number of portions of aerosol-generating substrate than there are heat sources. In a preferred embodiment, the device comprises precisely two heat sources.

In a further embodiment, during the step of heating the aerosol-generating substrate, the heating profile of the first heat source may be different from the heating profile of the second heat source. In the configuration described above, the temperature profiles of the first and second portions of the aerosol-generating substrate derive from the heating profiles of the first and second heat sources, respectively. Therefore, the differing heating profiles of the first and second heat sources will result in differing temperature profiles of the first and second portions of the aerosol-generating substrate.

The first and second heat sources may be independently controlled; that is, the first heat source may be controlled separately from the second heat source. In one such embodiment, the device may comprise a power source and controller which can provide power independently to each of the heat sources. Where the power source is an electrical power source, the controller may control the supply of electrical power from the electrical power source to the first heat source independently of the supply of electrical power from the electrical power source to the second heat source. By controlling the power supplied to each of the heat sources in use, the heating profiles of the heat sources can be controlled, thereby providing an aerosol-generating substrate with first and second portions which have more than one temperature profile.

The first and second heat sources may be portions of a single heating element which are capable of different heating profiles. Preferably, though, the first and second heat sources are physically separate units. In the case where the heat sources are electrically resistive heating elements, the heating elements may be supplied with separate electrical currents; that is, the heating elements might not be part of the same electrical circuit.

By using two heat sources it is possible to accurately control the temperature profiles of the first and second portions of the aerosol-generating substrate by controlling the heating profiles of each of the heat sources. Control of the heating profiles of the heat sources in turn controls the temperature profiles of the portions of the aerosol-generating substrate, as the temperature profiles derive from the heating profiles of the heat sources and the insulative property of the intervening space between heat sources and substrate.

Although the heating profiles of the heat sources induce the temperature profiles of the portions of the aerosol-generating substrate, the heating profiles and temperature profiles may not exactly correspond. For example: there may be "bleed" in the form of conduction of heat energy from one portion of the aerosol-generating substrate to another; there may be variations in conduction of heat energy from the heat sources to the substrate; there may be a lag between the change in the temperature profile of the aerosol-generating substrate and the change in the heating profile of the heat sources, depending on the heat capacity of the substrate.

In embodiments wherein the device comprises a controller, the controller may be programmed to control the heating profiles of the heat sources, such that the heating profiles of the heat sources induce prescribed temperature profiles in the first and second portions of the aerosol-generating substrate. For example, the controller may be programmed to control the current supplied to the heat sources such that the heat profiles of the heat sources (and therefore the induced temperature profiles of the first and second portions of the aerosol-generating substrate) differ in rate of change of temperature, in target temperature, by start time, or by any combination thereof. In particular, the controller may be programmed to control the heat profiles of the heat sources to induce any of the temperature profiles of portions of the aerosol-generating substrate specifically described above.

In a particular embodiment where the heat sources are electrically resistive heating elements, a current may be supplied to the first heat source before supplying a current to the second heat source. The second heat source may be "phased in" to generate further aerosol from the substrate after the first heat source has begun to generate aerosol from the substrate.

Although the heating profiles of the heat sources may be staggered, they invariably overlap. That is, where there are a plurality of heat sources, there will be at least one period of time in the session where more than one heat sources is supplying heat energy to the aerosol-generating substrate. In one example, where there are two heat sources, there will be at least one period of time in the session where both the first and second heat source supply heat energy to the aerosol-generating substrate. In particular, where each heat source is an electrically resistive heating element configured to receive a current from an electrical power source controlled by a controller, there will be at least one period of time in the session where both the first and second heat sources are supplied with a current.

In some embodiments, the first heat source (and consequently the first portion of the aerosol-generating substrate) is disposed closer to the mouth end of the device than the second heat source (and consequently the second portion of the aerosol-generating substrate). In a particular embodiment, the first heat source which is disposed closer to the mouth end than the second heat source begins to emit heat energy and thereby heat the first portion of the aerosol-generating substrate before the second heat source begins to emit heat energy and thereby heat the second portion.

Each of the heat sources preferably emits heat energy for a sustained period during a session. In particular, each of the heat sources emits heat energy for a sustained period with a duration of at least 25%, 50%, or 75% of the session. In one embodiment, once each heat source has begun to emit heat energy in the session, each heat source continues emitting heat energy until the end of the session, when the aerosol-generating substrate is depleted. Put another way, where each heat source is an electrically resistive heating element configured to receive a current from an electrical power source controlled by a controller, once each source has begun to receive a current from the electrical power source, it will continue to be supplied with a current until the end of the session, when the aerosol-generating substrate is depleted.

Emitting heat for a sustained period may mean that the device provides substantially consistent aerosol formation without the need to heat portions of the aerosol-generating substrate to a very high temperature, or without the need for the heat source to have a very high temperature. This may help to avoid overheating or charring of the aerosol-generating substrate. For example, in some embodiments, the temperature of a heat source disposed within the aerosol-generating device does not exceed 240° C. when in use. This ensures that the tobacco is not overheated.

Another aspect of the present invention is the device used to generate the aerosol. In one embodiment, the aerosol-generating device has a substrate or heating chamber having first and second heating zones. The heating chamber is generally in the form of a hollow cylindrical tube, into which the aerosol-generating substrate is inserted for heating in use. The chamber is configured such that when the substrate is inserted into the cavity, the first and second heating zones correspond to the first and second portions of the aerosol-generating substrate respectively. In a particular embodiment, the heating zones are aligned longitudinally along the heating chamber.

The device further comprises at least one heat source. In use, the first and second heating zones transfer heat energy from the at least one heat source to the first and second portions of the aerosol-generating substrate respectively. In some embodiments, the device comprises a first heat source and a second heat source. In such embodiments, the first and second heating zones correspond to the first and second heat sources.

Preferably, the first and second heating zones transfer heat energy to the external surface of the aerosol-generating substrate. That is, preferably neither the at least one heat source nor the first and second heating zones are disposed within the aerosol-generating substrate in use. This may allow for using a particularly easily removable and/or disposable aerosol-generating substrate with the aerosol-generating device.

In further embodiments, the device may comprise more than two heating zones. For example, the device may comprise three, four, five, or more than five heating zones. In these examples, the device may comprise any number of heat sources, as appropriate. It may be that there are a greater number of heating zones than there are heat sources.

The at least one heat source may be annular, or at least part-annular. In one embodiment, the heating element may be a thin-film heater. In another embodiment, where the heat source is annular, the aerosol-generating substrate is in the form of a rod. Preferably, the aerosol-generating substrate lies co-axially within the annulus of the heat source in use, especially where the aerosol-generating substrate is in the form of a rod.

In a preferred embodiment, the aerosol-generating device comprises precisely two heat sources, disposed longitudinally along the heating chamber. FIG. 1 is a cross section of the heating chamber when the substrate is disposed in the chamber. The aerosol-generating device comprises precisely two heat sources 102 and 104, disposed longitudinally along the heating chamber 100. In particular, the first heat source 102 is disposed closer to the mouth end 106 than the second heat source 104. The second heat source 104 is disposed closer to the distal end 108 than the first heat source 102. The aerosol-generating substrate 200 comprises a first portion 202 and a second portion 204. In use, the first heat source 104 supplies heat energy to the first portion 202 before the second heat source 104 supplies heat energy to the second portion 204.

Another method of controlling the temperature profiles of the first and second portions of the aerosol-generating substrate, which may be used in conjunction with, or as an alternative to, a plurality of heat sources with different heating profiles as discussed above, is the use of thermally insulative materials or components. In some embodiments, a thermally insulative material is disposed between the at least one heat source and the first and second heating zones, thereby at least partially inhibiting the transfer of heat from the at least one heat source to the aerosol-generating substrate in use. The insulative material or component is configured differently for the first and second heating zones, such that if substantially the same amount of heat energy is emitted from the at least one heat source in the direction of both heating zones, the first heating zone would nevertheless not transfer the same amount of heat energy to the first portion of the aerosol forming portion as the second heating zone would transfer to the second portion of the aerosol-generating substrate, so the temperature profiles of the portions would differ from each other. One example of such a configuration might be that an insulative material is disposed between the at least one heat source and the first heating zone, but there is no such insulative material between the at least one heat source and the second heating zone.

In a particular embodiment, the first and second portions of the aerosol-generating substrate are heated by a single heat source. That is, the differing temperature profiles of the first and second portions derive from the configuration of the insulative material alone.

Exemplary insulative materials include aerogels, sol-gels, or ceramics. For example, the insulative material may comprise glass, silica gel, calcium sulfate fibres or carbon filaments. The insulative component may be a layer of vacuum insulation—a layer which is bounded by a material providing an internal region which is evacuated to low pressure.

EXAMPLE

In an aerosol-generating device comprising:
a tobacco rod comprising first and second portions;
a first and second electrically resistive heating element corresponding to the respective portions of the rod;
an electrical power source;
a plurality of RTDs; and
a controller for controlling the power supplied to the first and second resistive heating elements;
the controller was programmed to carry out the following:
 When the device is switched on, provide power to the first electrically resistive heating element to heat the element to a temperature of 240° C. immediately; once the element reaches 240° C., maintain it at that temperature;
 75 seconds from turning the device on, provide power to the second electrically resistive heating element to heat the element to a temperature of 160° C.; once the element reaches 160° C., maintain it at that temperature;
 135 seconds from turning the device on, provide power to the second electrically resistive heating element to heat the element to a temperature of 240° C.; once the element reaches 240° C., maintain it at that temperature;
 145 seconds from turning the device on, lower the temperature of the first electrically resistive heating element to 135° C.
 280 seconds from turning the device on, shut down.

Figure 2:
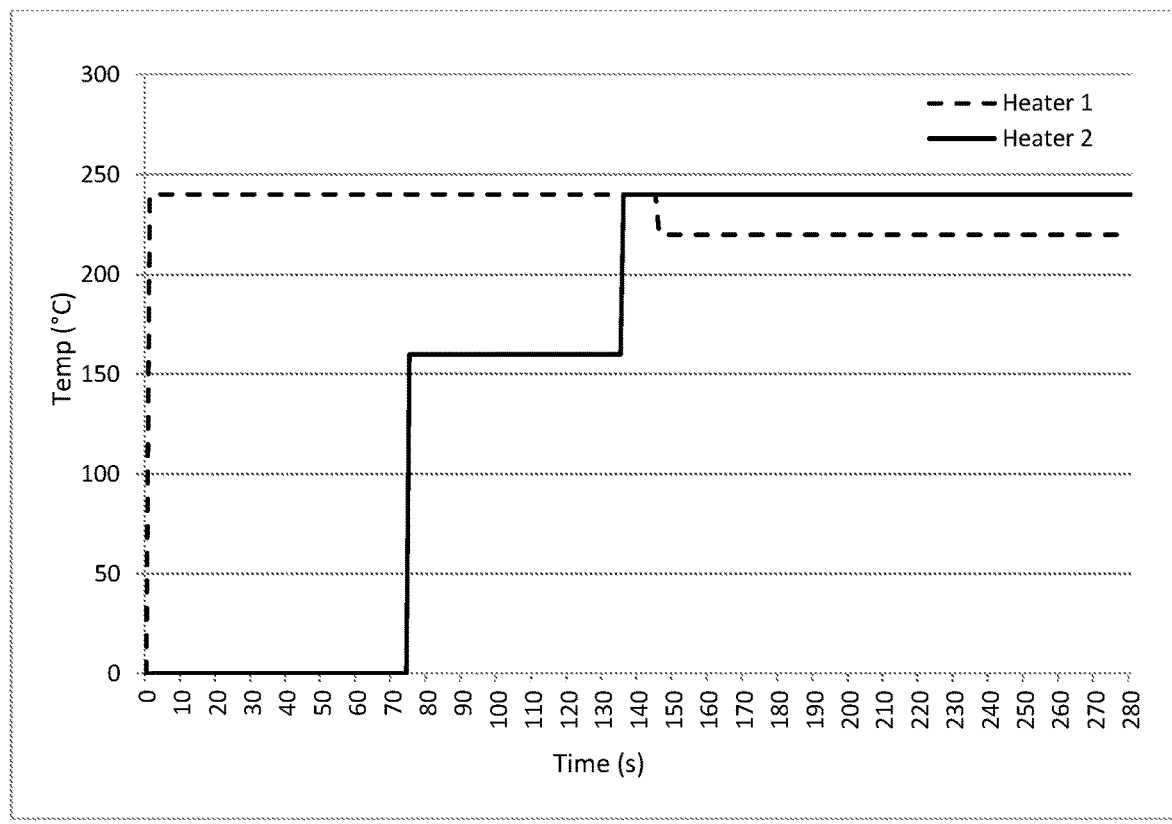
FIG. 2 is a graph relating to an embodiment according to the present invention, showing programmed heating profiles of two heat sources in an aerosol-generating device whilst heating an aerosol-generating substrate.
Figure 3:
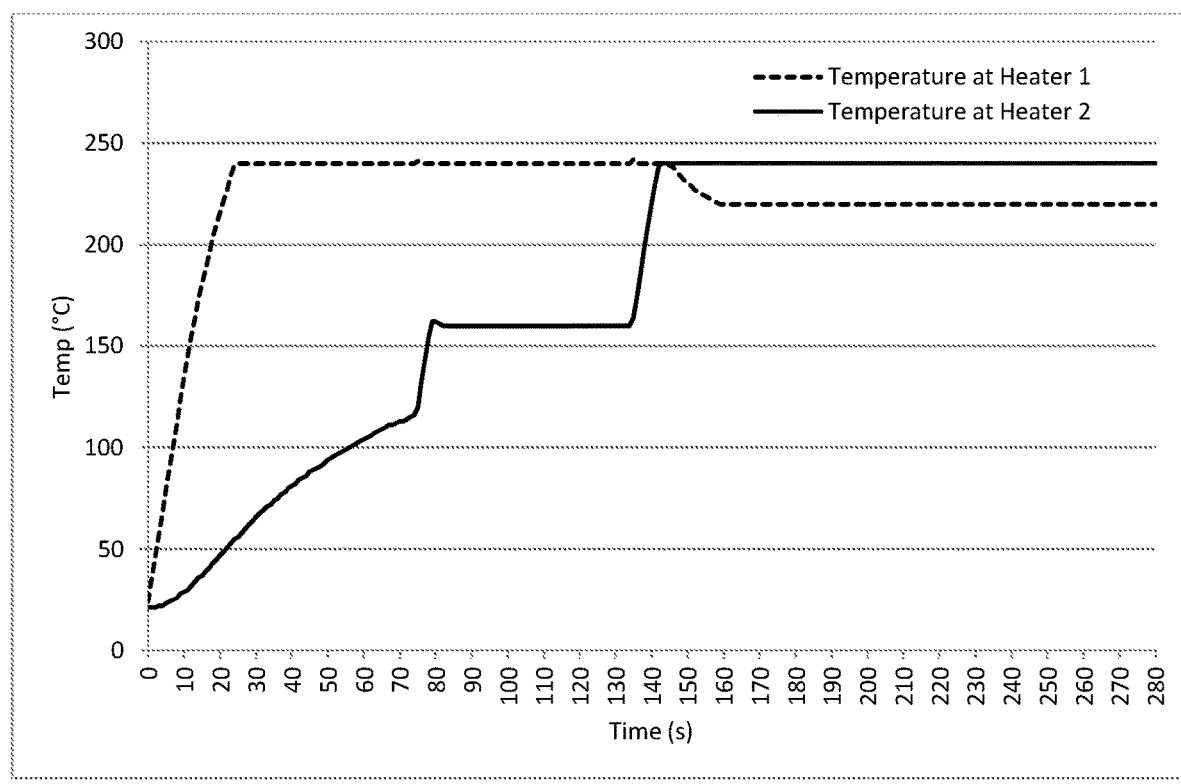
FIG. 3 is a graph relating to an embodiment according to the present invention, showing temperature profiles of two portions of an aerosol-generating substrate whilst being heated by two heat sources in an aerosol-generating device.

FIG. 2 shows a heater trace of the two heating elements as programmed. FIG. 3 shows a temperature trace of the heating elements as recorded by the RTDs corresponding to the two heating elements. This second trace takes into account the time taken for the heating elements to reach the prescribed temperature, and the rise of temperature in the second portion of the aerosol-generating substrate despite only the first heating element heating the first portion of the substrate.

The various embodiments described herein are presented only to assist in understanding and teaching the claimed features. These embodiments are provided as a representative sample of embodiments only, and are not exhaustive and/or exclusive. It is to be understood that advantages, embodiments, examples, functions, features, structures, and/or other aspects described herein are not to be considered limitations on the scope of the invention as defined by the claims or limitations on equivalents to the claims, and that other embodiments may be utilised and modifications may be made without departing from the scope of the claimed invention. Various embodiments of the invention may suitably comprise, consist of, or consist essentially of, appropriate combinations of the disclosed elements, components, features, parts, steps, means, etc., other than those specifically described herein. In addition, this disclosure may include other inventions not presently claimed, but which may be claimed in future.

The invention claimed is:

1. A method of generating aerosol from an aerosol-generating substrate using an aerosol-generating device comprising a first heat source and a second heat source disposed to heat, but not burn, the aerosol-generating substrate in use and are not integral to the aerosol-generating substrate;
 wherein the aerosol-generating substrate comprises first and second portions and there is no physical separation between the portions; and
 wherein the first and second heat sources are susceptors capable of being inductively heated;
 wherein the first heat source is disposed to heat, but not burn, the first portion of the aerosol-generating substance in use;
 wherein the second heat source is disposed to heat, but not burn, the second portion of the aerosol-generating substance in use; and
 wherein the first and second heat sources are independently controllable;
 the method comprising the steps of:
 heating the aerosol-generating substrate in the aerosol-generating device over a period of time corresponding to a session of use, so that a temperature profile of the first portion of the aerosol-generating substrate during heating is different from a temperature profile of the second portion of the aerosol-generating substrate, wherein the temperature profiles of the first and second portion differ in target temperature.

2. A method according to claim 1, wherein the heating over the period of time corresponding to the session of use has a duration of at least 2 minutes, and the temperature of each of the first and second portions of the aerosol-generating substrate is greater than 100° C. for at least half the duration of the heating of the period of time corresponding to the session of use.

3. A method according to claim 1, in which during said heating, the heating profile of the first heat source is different from the heating profile of the second heat source.

4. A method according to claim 1, wherein the first heat source begins to heat the aerosol-generating substrate before the second heat source begins to emit heat energy.

5. A method according to claim 1, wherein the device has a mouth end and a distal end, and the first portion of the aerosol-generating substrate is disposed closer to the mouth end of the device than the second portion of the aerosol-generating substrate.

6. A method according to claim 1, wherein the aerosol-generating substrate comprises a tobacco component.

7. A method according to claim 1, wherein the aerosol-generating device is a Tobacco Heating Product.

8. A method according to claim 1, wherein the aerosol-generating substrate comprises a tobacco component in an amount of from 60 to 90% by weight of the aerosol-generating substrate, a filler in an amount of 0 to 20% by weight of the aerosol-generating substrate, and an aerosol generating agent in an amount of from 10 to 20% by weight of the tobacco composition.

9. A method according to claim 1, wherein the temperature of the first heat source and/or the second heat source does not exceed 240° C.

10. A method according to claim 1, wherein the device comprises a power source for providing power to the first heat source and the second heat source.

11. A method according to claim 1, wherein the aerosol-generating device provides a substantially constant puff profile from the aerosol-generating substrate.

12. The method according to claim 1, wherein the temperature profiles of the first and second portion differ in start time and one or both of rate of change of temperature and difference in target temperature.

13. The method according to claim 1, wherein the target temperature of the first and/or second heat source can be selectively controlled.

14. An aerosol-generating device comprising:
a heating chamber having first and second heating zones disposed to heat, but not burn, an aerosol: generating substrate in use, the first heating zone comprising a first heat source and the second heating zone comprising a second heat source, wherein the first heat source and the second heat source are not integral to the aerosol-generating substrate;
wherein the first and second heat sources are susceptors capable of being inductively heated;
wherein the first heat source is disposed to heat, but not burn, the first portion of the aerosol-generating substance in use;
wherein the second heat source is disposed to heat, but not burn, the second portion of the aerosol-generating substance in use;
wherein the device is configured such that, in use, the heating profile of the first heat source is different from the heating profile of the second heat source, and
wherein the first and second heat sources are independently controllable.

* * * * *